United States Patent

Plath et al.

[11] Patent Number: 5,981,758
[45] Date of Patent: Nov. 9, 1999

[54] PREPARATION OF SACCHARINCARBONYL HALIDES

[75] Inventors: Peter Plath, Frankenthal; Wolfgang von Deyn, Neustadt; Michael Rack, Heidelberg; Ulf Misslitz, Neustadt, all of Germany

[73] Assignee: BASF Aktiengesellschaft, Ludwigshafen, Germany

[21] Appl. No.: 09/275,802

[22] Filed: Mar. 25, 1999

[30] Foreign Application Priority Data

Mar. 25, 1998 [DE] Germany .............. 198 13 014

[51] Int. Cl.⁶ .................................. C07D 275/06
[52] U.S. Cl. ............................. 548/210; 548/211
[58] Field of Search .................. 548/210, 211

[56] References Cited

U.S. PATENT DOCUMENTS

| | | | |
|---|---|---|---|
| 4,744,425 | 5/1988 | Hentschel | 175/73 |
| 5,716,906 | 2/1998 | Plath et al. | 504/269 |
| 5,723,415 | 3/1998 | Plath et al. | 504/269 |

FOREIGN PATENT DOCUMENTS

| | | |
|---|---|---|
| 688562 | 3/1998 | Australia . |
| 3607343 | 9/1986 | Germany . |
| 96/05182 | 2/1996 | WIPO . |
| 96/05184 | 2/1996 | WIPO . |
| 96/05197 | 2/1996 | WIPO . |
| 96/05198 | 2/1996 | WIPO . |
| 98/40366 | 9/1998 | WIPO . |

*Primary Examiner*—Laura L. Stockton
*Attorney, Agent, or Firm*—Keil & Weinkauf

[57] ABSTRACT

A process for preparing saccharincarbonyl halides of the formula 1

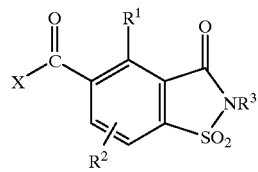

where:
  X is halogen,
  $R^1$, $R^2$ are each hydrogen, $C_1$–$C_6$-alkyl, $C_3$–$C_8$-cycloalkyl, $C_1$–$C_4$-alkoxy, optionally $C_1$–$C_4$-alkyl-, fluorine- or $C_1$–$C_4$-alkoxy-substituted benzyl or phenyl,
  $R^3$ is hydrogen, $C_1$–$C_6$-alkyl, $C_3$–$C_8$-cycloalkyl or phenyl or benzyl which is optionally mono- or polysubstituted by $C_1$–$C_4$-alkyl, halogen, $C_1$–$C_4$-haloalkyl or $C_1$–$C_4$-alkoxy,
by reaction of an isophthalylsulfonamide 2 with an inorganic acid halide to give the saccharincarbonyl halide 1

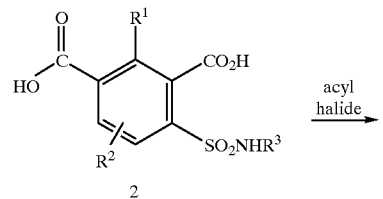

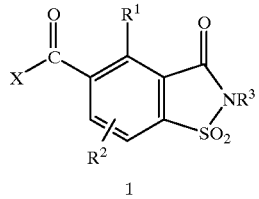

is described.

10 Claims, No Drawings

PREPARATION OF SACCHARINCARBONYL HALIDES

The present invention relates to a process for preparing saccharincarbonyl halides of the formula 1

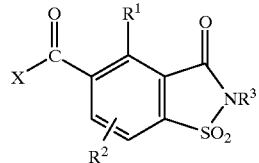

where:
X is halogen,
$R^1$, $R^2$ are each hydrogen, $C_1$–$C_6$-alkyl, $C_3$–$C_8$-cycloalkyl, $C_1$–$C_4$-alkoxy, optionally $C_1$–$C_4$-alkyl-, fluorine- or $C_1$–$C_4$-alkoxy-substituted benzyl or phenyl,
$R^3$ is hydrogen, $C_1$–$C_6$-alkyl, $C_3$–$C_8$-cycloalkyl or phenyl or benzyl which is optionally mono- or polysubstituted by $C_1$–$C_4$-alkyl, halogen, $C_1$–$C_4$-haloalkyl or $C_1$–$C_4$-alkoxy.

Furthermore, the present invention relates to processes for preparing the intermediates from which the saccharincarbonyl halides 1 can be prepared.

The saccharincarbonyl halides 1 are important intermediates in the preparation of herbicidally active compounds as described, for example, in WO 96/05182, WO 96/05197, WO 96/95198 and P 19709697.2.

In these applications, herbicidal saccharin derivatives are described which are linked via a carbonyl group at the aromatic with a cyclohexane-1,3-dione ring, a hydroxypyrazole ring, an isoxazole ring or a cyclohexane-1,3,5-trione ring.

Processes for preparing saccharin derivatives are known. Thus, DE 36 07 343 describes a process for preparing 4-hydroxy-1,2-benzisothiazol-3(2H)-one 1,1-dioxide where substituted 1,2-benzisothiazole 1,1-dioxides are nucleophilically substituted by alkoxides. Another intermediate that has been described is 4-chlorosaccharin-5-carboxylic acid which was prepared by oxidation of 3-chloro-2,4-dimethylbenzenesulfonamide with potassium permanganate, i.e. the two carboxyl functions were introduced by oxidation of two methyl groups, with concomitant oxidative ring closure. It is a disadvantage of this process that, if a plurality of functional groups is present, no selective oxidation is possible.

WO 96/05184 describes a process for preparing saccharincarboxylic acids and esters by reaction of bromine- or iodine-substituted saccharin derivatives or open-chain carbonamide-sulfonamide derivatives thereof with carbon monoxide and water or an alcohol in the presence of a base and a transition metal catalyst.

This process has the disadvantage that, if aryl iodides are used, undesirable by-products are formed.

It is an object of the present invention to provide a novel process for preparing saccharincarbonyl halides of the formula 1 which uses easily obtainable starting materials and which does not have the disadvantages of the processes of the prior art.

Furthermore, we have found a process for preparing the isophthalylsulfonamide 2 by hydrolysis of a 5-cyanosaccharin 3 with aqueous alkali metal hydroxide solution

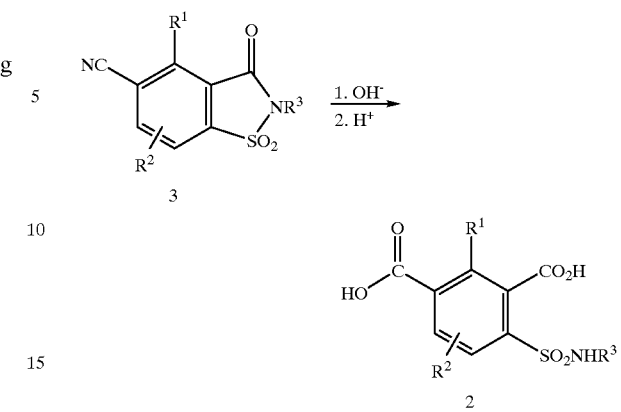

and subsequent addition of an acid.

Additionally, we have found a process for preparing the 5-cyanosaccharin 3 by reaction of a dicyanobenzenesulfonyl chloride 4 with an amine of the formula $R^3$-$NH_2$ to give the iminosaccharin derivative 5

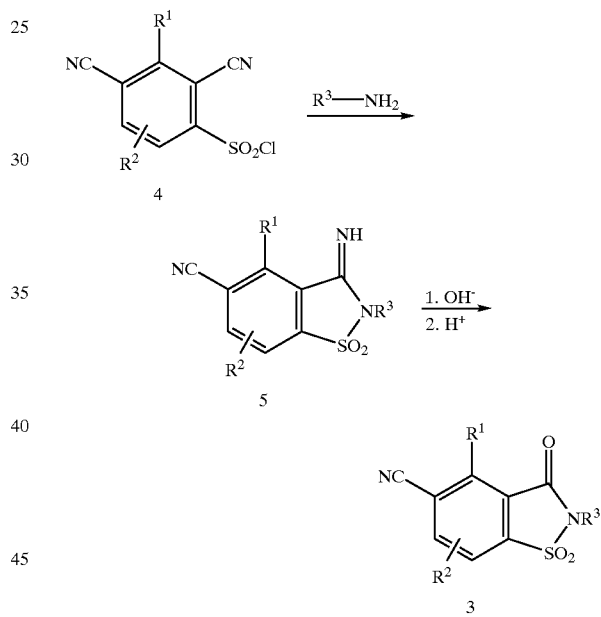

and subsequent acid hydrolysis.

We have found that this object is achieved by a process for preparing saccharincarbonyl halides of the formula 1

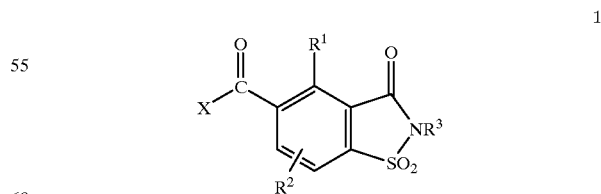

where:
X is halogen,
$R^1$, $R^2$ are each hydrogen, $C_1$–$C_6$-alkyl, $C_3$–$C_8$-cycloalkyl, $C_1$–$C_4$-alkoxy, optionally $C_1$–$C_4$-alkyl-, fluorine- or $C_1$–$C_4$-alkoxy-substituted benzyl or phenyl, $R^3$ is hydrogen, $C_1$–$C_6$-alkyl, $C_3$–$C_8$-cycloalkyl or phenyl or benzyl which is optionally mono- or polysubstituted by $C_1$–$C_4$-alkyl, halogen, $C_1$–$C_4$-haloalkyl or $C_1$–$C_4$-alkoxy, which comprises reacting an isophthalylsulfonamide 2 with an inorganic acid halide to give the saccharincarbonyl halide 1

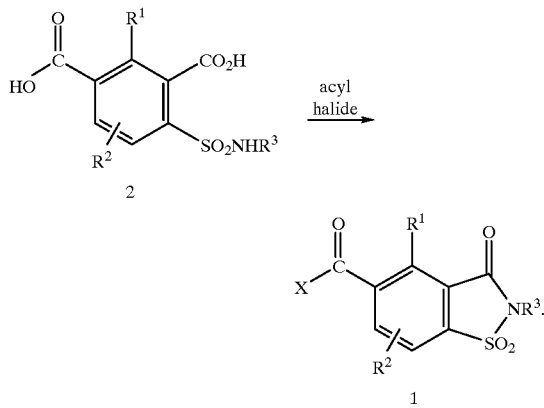

The organic molecule moieties mentioned for the substituents X and $R^1$–$R^3$ or as radicals on phenyl and benzyl rings are collective terms for individual enumerations of the individual group members. All hydrocarbon chains, i.e. all alkyl, haloalkyl, cycloalkyl and alkoxy moieties, may be straight-chain or branched. Unless stated otherwise, halogenated substituents preferably carry one to five identical or different halogen atoms. The term halogen denotes in each case fluorine, chlorine, bromine or iodine.

Examples of other meanings are:

$C_1$–$C_4$-alkyl, and the alkyl moieties of $C_1$–$C_4$-alkylcarbonyl: methyl, ethyl, n-propyl, 1-methylethyl, butyl, 1-methylpropyl, 2-methylpropyl and 1,1-dimethylethyl;

$C_1$–$C_6$-alkyl, and the alkyl moieties of $C_1$–$C_6$-alkoxy-$C_1$–$C_6$-alkyl and $C_1$–$C_6$-alkylcarbonyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy, and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_3$–$C_8$-cycloalkyl: cyclopropyl, cyclobutyl, cyclopentyl, cyclohexyl, cycloheptyl and cyclooctyl.

The process according to the invention is preferably used to prepare saccharincarbonyl halides of the formula 1 where:

X is chlorine, $R^1$, $R^2$ are each hydrogen, $C_1$–$C_6$-alkyl, $C_1$–$C_4$-alkoxy or optionally $C_1$–$C_4$-alkyl-, fluorine- or $C_1$–$C_4$-alkoxy-substituted benzyl, $R^3$ is hydrogen, $C_1$–$C_6$-alkyl, $C_3$–$C_8$-cycloalkyl, phenyl or benzyl.

Preference is furthermore given to preparing compounds 1 where

X is chlorine, $R^1$, $R^2$ are each hydrogen, methyl, ethyl or methoxy, $R^3$ is hydrogen, methyl, ethyl, isopropyl, cyclohexyl, benzyl or phenyl.

Particular preference is given to preparing compounds 1 where

X is chlorine, $R^1$ is methyl, ethyl or methoxy, $R^2$ is hydrogen, $R^3$ is hydrogen, methyl, ethyl, benzyl or phenyl.

The entire process for preparing the saccharincarbonyl halides 1 entails the following steps:

Step 1

The sequence of the synthesis starts with the preparation of the 3-aminobenzonitrile 7 from the 3-haloaniline 6 and CuCN,

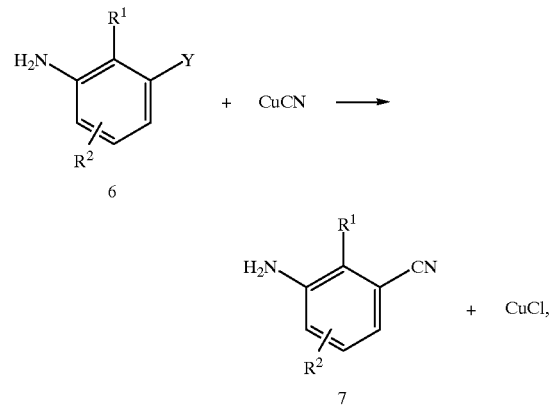

where Y is Cl, Br or I, preferably Cl. Suitable solvents are organic solvents such as, for example, N-methylpyrrolidone, pyridine, dimethylformamide or tetramethylurea.

Preference is given to using N-methylpyrrolidone. The reaction is carried out at 90–240° C., preferably at 220–230° C. If N-methylpyrrolidone is used, the reaction is preferably carried out at the boiling point of the solvent. The reaction time is from 6 to 18 h, preferably from 8 to 12 h.

If DMF or pyridine is employed, it is advantageous to use temperatures of up to 240° C., under autogenous pressure.

Step 2

The sulfur atom of what is to become the saccharin ring is introduced by thiocyanatogenation of 7 with thiocyanogen:

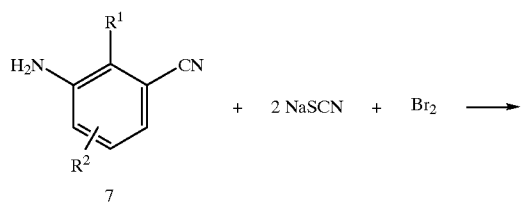

+ 2 NaSCN + Br$_2$ ⟶

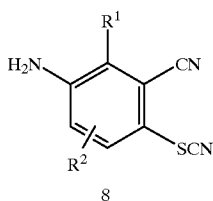

The reaction is carried out in a manner known per se at −20° C.−+25° C., preferably at −5° C.−+5° C. Suitable solvents are alcohols such as methanol or ethanol, but also acetic acid, propionic acid or isobutyric acid. The preferred solvent is methanol to which some potassium bromide has been added for stabilization.

Step 3

The 3-cyano-4-thiocyanatoaniline 8 obtained in this manner is then converted into the 4-thiocyanatoisophthalodinitrile 9 in a Sandmeyer reaction:

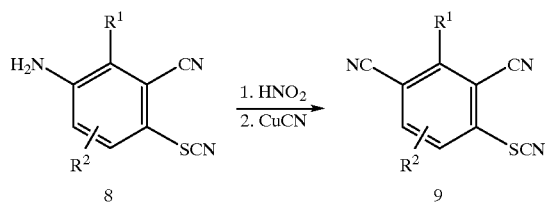

Suitable solvents are organic solvents such as, for example, aceic acid or mixtures of acetic acid and conc. hydrochloric acid. Preference is given to using the mixture glacial acetic acid/conc. hydrochloric acid=2.5:1. The reaction is carried out at −5–25° C., preferably at −5–+5° C. The reaction time is from 2 to 16 h, preferably from 1 to 3 h. In this reaction, the dinitrile 9 is obtained as a complex with Cu(I) and is liberated by treatment with O$_2$ in conc. hydrochloric acid.

Step 4

The dinitrile 9 is subsequently converted into 2,4-dicyanothiophenol 10 using aqueous sodium sulfide:

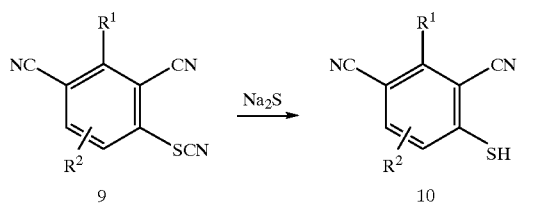

Suitable solvents are organic solvents such as, for example, methanol or ethanol as a mixture with water.

Preference is given to using aqueous methanol. The reaction is carried out at 5–30° C., preferably at 15–25° C. The reaction time is from 2 to 8 h, preferably from 2 to 3 h.

Step 5

Chlorination of 10 leads to 2,4-dicyanobenzenesulfonyl chloride 4:

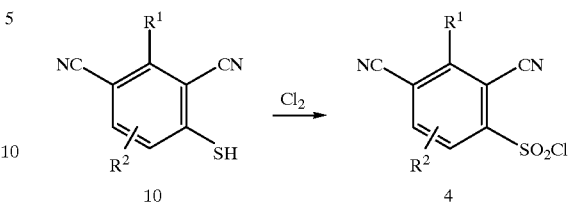

Suitable solvents are organic solvents such as, for example, dichloromethane, 1,2-dichloroethane, chlorobenzene or acetic acid.

Preference is given to using a mixture of acetic acid and dichloromethane. The reaction is carried out at 0–60° C., preferably at 25–50° C. The reaction time is from 2 to 10 h, preferably from 4 to 6 h, depending on the rate at which the chlorine is introduced. The amount of chlorine to be introduced in mol is at least five times the amount of the thiophenol 10 used. In practice, however, an excess of chlorine is used which is determined by the fact that an intermediate solid redissolves on further addition of chlorine.

Step 6

Action of an amine of the formula R$^3$-NH$_2$ affords (instead of the expected isophthalodinitrilesulfonamide) the iminosaccharin derivative 5 which is cleaved by acid hydrolysis into the cyanosaccharin 3:

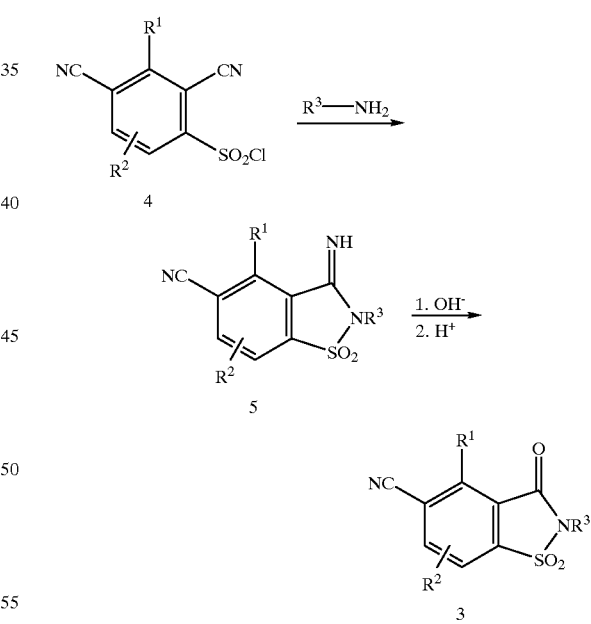

Suitable solvents are organic solvents such as, for example, tetrahydrofuran, dioxane or acetonitrile.

Preference is given to using tetrahydrofuran (THF) as a mixture with water. The reaction is carried out at 0–40° C., preferably at 4–25° C. The reaction time is from 1 to 16 h, preferably from 2 to 8 h.

Ammonia, $C_1$–$C_6$-alkylamines, $C_3$–$C_8$-cycloalkylamines and aniline or benzylamine which is optionally mono- or polysubstituted by $C_1$$C_4$-alkyl, halogen, $C_1$–$C_4$-haloalkyl or $C_1$–$C_4$-alkoxy are used as amines.

Suitable $C_1$–$C_6$-alkylamines are methylamine, ethylamine, isopropylamine, n-butylamine and isobutylamine.

Preference is given to using methylamine, ethylamine and isobutylamine.

Suitable $C_3$–$C_8$-cycloalkylamines are cyclopropylamine, cyclobutylamine, cyclopentylamine, cyclohexylamine, cycloheptylamine and cyclooctylamine.

Preference is given to using cyclopentylamine and cyclohexylamine.

Suitable substituted benzylamines or anilines are 2-chlorobenzylamine, aniline and 2-methylaniline, 3-chloroaniline, 3-$CF_3$-aniline.

Preference is given to using aniline and benzylamine.

Very particularly preferred amines are ammonia, methylamine, ethylamine, isobutylamine and aniline.

The acid hydrolysis is carried out using organic or inorganic acids. Preference is given to using acetic acid.

Step 7

Hydrolysis of 3 with aqueous alkali metal hydroxide solution and subsequent acidification with an acid affords the isophthalic acid 2:

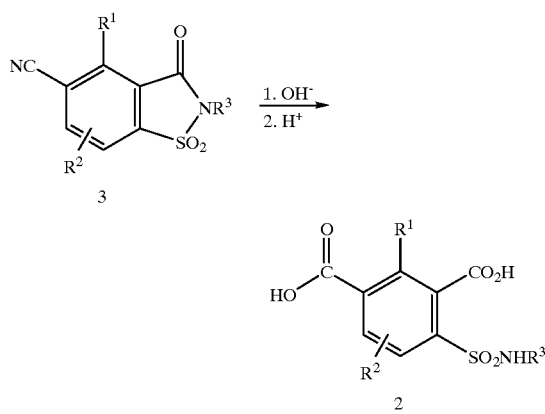

The hydrolysis of 3 is carried out using 20–25 percent NaOH or KOH at 90–100° C. Preference is given to using 20 percent NaOH or KOH. The reaction time depends on the end of the evolution of ammonia and is from 6 to 16 h, and from 6 to 8 h if 20 percent KOH is used.

Acidification is carried out using an inorganic or organic acid. Preference is given to using conc. hydrochloric acid.

Step 8

Heating of 2 with an acid halide affords the saccharin-5-carbonyl halide 1

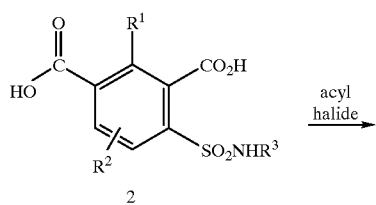

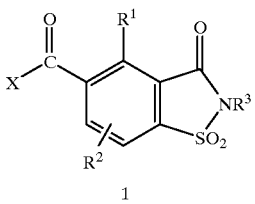

The solvent used is either excess acid chloride or toluene, chlorobenzene, xylenes or 1,2-dichloroethane.

The acid halides used are inorganic acid chlorides such as thionyl chloride, phosphorus oxychloride, oxalyl chloride or phosgene.

Preference is given to using thionyl chloride in the solvent toluene. The temperature is 25–130° C.

Preparation Examples

Step 1: 3-Amino-2-methylbenzonitrile 283 g (2.0 mol) of 3-chloro-2-methylaniline are dissolved in 250 ml of N-methylpyrrolidone and admixed with 200 g (2.23 mol) of CuCN. The reaction mixture is subsequently stirred under $N_2$ and at 225° C. for six hours. After cooling to 100° C., the reaction mixture is poured into 2.5 l of 25 percent ammonia solution and stirred at 25° C. for one hour. During this time, the atmospheric oxygen oxidizes the Cu(I) nitrile complex of the product to a water-soluble Cu(II) salt, which is evident by the formation of the intensively blue tetramine complex. Some of the CuCl remains undissolved as a white solid and can be easily removed by filtration with suction. The filtrate is extracted with approximately 2 l of methyl tert-butyl ether and then washed with ammonia water and finally three times with water. The organic phase is dried over sodium sulfate and concentrated, affording 255 g (89% yield of crude product) of a dark oil which can be purified by recrystallization from cyclohexane/toluene (5:1).

Yield after recrystallization: 205 g (78% of theory), m.p.: 93–94° C.

Step 2: 2-Methyl-3-cyano-4-thiocyanatoaniline 30 g of NaBr are suspended in 1500 ml of methanol, and 212.8 g (1.52 mol) of 3-amino-2-methylbenzonitrile and 246 g (3 mol) of sodium thiocyanate are added. The mixture is then cooled to −5° C., and 243 g (1.52 mol) of bromine are slowly added dropwise at −5 to 0° C. After some time, a precipitate forms. The reaction has ended after 16 hours of stirring at 25° C.

Work-up

The reaction mixture is poured into 2.5 l of water and the precipitated solid (132 g) is filtered off with suction. The filtrate is extracted using MTBE (methyl tert-butyl ether) and gives, after drying and concentration of the extract, a further 144 g of crude product. Both solid fractions are combined and recrystallized from ethanol.

Yield after recrystallization: 218 g (76% of theory).

The product (m.p.: 143° C.) is pure according to IR and NMR.

When the experiment was repeated, a yield of 80% was obtained.

Step 3: 2-Methyl-4-thiocyanatoisophthalodinitrile

With heating, 189 g (1 mol) of 2-methyl-3-cyano-4-thiocyanoaniline are dissolved in 1 kg of glacial acetic acid, and 400 g (4 mol) of conc. HCl and, after 15 min of stirring, 400 ml of water are then added, resulting in a finely distributed suspension of the hydrochloride. The mixture is stirred for a short time (15 to 30 min), and the solution of 69 g (1 mol) of sodium nitrite in 140 ml of water is then slowly added dropwise at −5–0° C. In a separate stirred flask, 245 g (5 mol) of NaCN are dissolved in a mixture of 1.5 l of water and 136 g (2 mol) of 25 percent ammonia water, and 250 g (1 mol) of $CuSO_4.5\ H_2O$ are added, resulting in the formation of the dark solution of a Cu(I) cyano complex. The diazonium solution which had been prepared beforehand and which is maintained at 0° C. is then quickly added dropwise at 25° C. to the Cu complex, and the temperature is allowed to rise to 40° C. in the process. Nitrogen evolves. After the evolution of gas has ended, stirring is continued for another 30 min.

Work-up

The product is present as a solid (nitrile complex with Cu(I)). Breaking down this complex with atmospheric oxygen in ammoniacal solution is not possible, since the thiocyanato radical is converted into the disulfide radical in the process.

The precipitated solid is filtered off with suction and washed three times with water. The filtrate contains product which has not been complexed and is therefore extracted with 2 l of methylene chloride. The solid is then charged in a stirred vessel and admixed with 1 l of conc. HCl. The methylene chloride extract is subsequently added, and the mixture is stirred for 15 minutes. The organic phase is separated off, components that have not dissolved are filtered off and the organic lower phase is washed three times with water and, after drying over sodium sulfate, concentrated. To remove undesirable components, the crude product is dissolved in ethyl acetate, undissolved particles are filtered off and the solution is subsequently concentrated. Yield: 170 g (85% of theory).

According to IR and NMR, the product (m.p.: 93° C.) is >95% pure and can be used without any further purification for further reactions.

Step 4: 3-Methyl-2,4-dicyanothiophenol 170 g (0.85 mol) of 2-methyl-4-thiocyanoisophthalonitrile are dissolved in 850 ml of methanol, a solution of 110.5 g (0.85 mol) of sodium sulfide (60 percent) in 425 ml of water is added at 25–35° C., and the mixture is stirred for a further three hours at room temperature. The mixture is then admixed with 1000 ml of water and extracted with methyl tert-butyl ether (MTBE) to remove all neutral components. The aqueous phase is adjusted to pH 1 by acidification with conc. HCl and the thiophenol is extracted with methylene chloride. The extract is washed three times with water and the organic phase is separated off, dried over sodium sulfate and concentrated. Drying of the residue under oil pump vacuum gives 150 g (99% of theory) of an orange solid, which is pure according to NMR.

The thiophenol is almost odorless at room temperature, this being characteristic for thiophenol having electron-attracting substituents. For the same reason, the compound is only very slowly oxidized to the disulfide on exposure to air.

Step 5: 2,4-Dicyano-3-methylbenzenesulfonyl chloride 116 g (0.67 mol) of 2,4-dicyano-3-methylthiophenol are dissolved in a mixture of 900 ml of acetic acid and 200 ml of methylene chloride, 48 g (2.67 mol) of water are added and a strong stream of chlorine gas is introduced at 25–50° C. over a period of four hours in such a manner that hardly any waste gas escapes at the bubble counter. A solid transiently precipitates from the solution, this solid redissolving in the further course of the chlorination. After the solid is completely dissolved, chlorine is introduced for a further 15 min (approximately), and the mixture is then allowed to cool, briefly flushed with nitrogen and then concentrated at 50° C. on a rotary evaporator. The residue, cooled to 25° C. and still liquid, is taken up in methylene chloride, washed with ice-water, dried over sodium sulfate and concentrated. 150 g (93% of theory) of an oil are isolated.

$^1$H NMR (CDCl$_3$, 270 MHz) δ [ppm]: 8.25 (d,1H), 8.15 (d,1H), 2.95 (s,3H) IR (cm$^{-1}$): 2220, (CN), 1385, 1170 (both for SO$_2$Cl)

Step 6:

6.1 3-Imino-2,4-dimethyl-5-cyanosaccharin

A solution of 168 g (3.5 mol) of 40 percent aqueous methylamine in 500 ml of THF is initially charged, and a solution of 150 g (0.62 mol) of 2,4-dicyano-3-methylsulfonyl chloride in 250 ml of THF is added dropwise at 25° C. while cooling with ice. The mixture is stirred at room temperature for 6 hours, and the THF and excess methylamine is then removed on a rotary evaporator. The residue is subsequently stirred twice with 1 l of dilute (1 percent) HCl. An orange solid is isolated which is used without any further purification for hydrolysis.

6.2 2,4-Dimethyl-5-cyanosaccharin

The water-moist solid (about 0.6 mol) obtained above is dissolved in 1 l of glacial acetic acid and heated at the boil for three hours. The mixture is subsequently evaporated to dryness, taken up in 1 l of methylene chloride and extracted three times with water to remove ammonium acetate. The organic phase is dried over sodium sulfate and the solvent is removed, giving a solid.

Crude yield: 126 g (86% of theory), m.p. 125° C. According to NMR, the product is sufficiently pure for the following reaction. The compound can be recrystallized from cyclohexane, its m.p. then being 160° C.

$^1$H NMR (CDCl$_3$, 270 MHz) δ [ppm]: 8.08 (d,1H), 7.85 (d,1H) 3.25 (s,3H, for NCH$_3$), 3.0 (s,3H)

Step 7: Hydrolysis to give 2-methyl-4-(N-methylsulfamoyl) isophthalic acid 127.4 g (0.54 mol) of 2,4-dimethyl-5-cyanosaccharin are suspended in a mixture of 248.4 g (2.15 mol) of 50 percent KOH and 250 ml of water, and the mixture is heated at the boil for 8 hours. Ammonia escapes via the condenser and can be detected by moist pH paper.

For work-up, the mixture is diluted with 500 ml of water and extracted with diethyl ether, and the organic phase is discarded. The alkaline aqueous phase is then adjusted to pH 1 using conc. HCl, saturated with NaCl and extracted three times with a mixture of ethyl acetate/THF=2:1. The organic phase is dried over sodium sulfate and then evaporated to dryness. According to IR and $^1$H-NMR, the residue (132 g, approximately 89% of theory) is 2-methyl-4-(N-methylsulfamoyl)isophthalic acid. The crude product (m.p. 156–158° C.) does not have to be purified any further for conversion into the saccharincarbonyl chloride. The melting point of the pure compound is 180° C.

IR (cm$^{-1}$): 3306, 3159, 1740, 1714, 1330, 1295, 1266, 1241, 1161

Step 8: 2,4-Dimethylsaccharin-5-carbonyl chloride 132 g (0.484 mol) of 2-methyl-4-(N-methylsulfamoyl) isophthalic acid are suspended in 600 ml of toluene and admixed with 0.5 g of DMF as catalyst. Without cooling (at 25–50° C.), 173 g (1.453 mol) of thionyl chloride are then added from a dropping funnel, and the mixture is subsequently heated at the boil until the evolution of waste gas has ceased; this is the case after about four hours.

After cooling to 50° C. over sodium sulfate, the product mixture is filtered off with suction to remove undissolved components. The filtrate is then concentrated under reduced pressure. Crude yield: 115 g (87% of theory). The compound can be recrystallized from toluene/cyclohexane=4:1, its m.p. is then 172° C. Yield after recrystallization: 92.2 g (78% of theory)

$^1$H NMR (CDCl$_3$, 270 MHz) δ [ppm]: 8.45 (d,1H), 7.95 (d,1H) 3.25 (s,3H, for NCH$_3$), 3.0 (d,3H)

The following compounds are obtained in a similar manner:

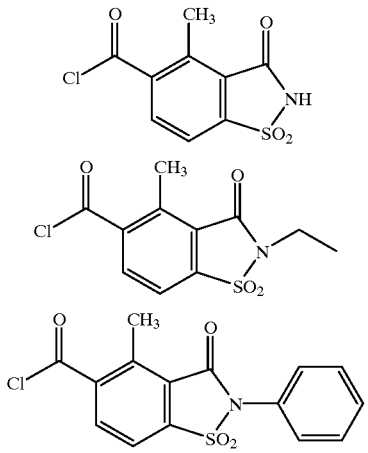

From the saccharincarbonyl halides of the invention, the corresponding saccharincarboxylic acids and the saccharincarboxylic esters can be prepared by hydrolysis with, for example, aqueous sodium bicarbonate and by reaction with alkoxides, respectively.

We claim:

1. A process for preparing saccharincarbonyl halides of the formula 1

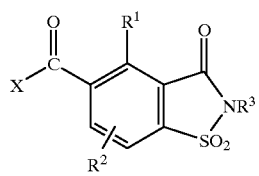

where:

X is halogen,

R$^1$, R$^2$ are each hydrogen, C$_1$–C$_6$-alkyl, C$_3$–C$_8$-cycloalkyl, C$_1$–C$_4$-alkoxy, optionally C$_1$–C$_4$-alkyl-, fluorine- or C$_1$–C$_4$-alkoxy-substituted benzyl or phenyl, R$^3$ is hydrogen, C$_1$–C$_6$-alkyl, C$_3$–C$_8$-cycloalkyl or phenyl or benzyl which is optionally mono- or polysubstituted by C$_1$–C$_4$-alkyl, halogen, C$_1$–C$_4$-haloalkyl or C$_1$–C$_4$-alkoxy, which comprises reacting an isophthalylsulfonamide 2 with an inorganic acid halide to give the saccharincarbonyl halide 1

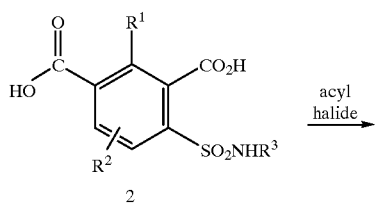

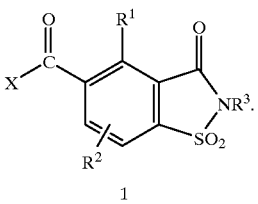

2. A process as claimed in claim 1, wherein the isophthalylsulfonamide 2 is prepared by hydrolysis of a 5-cyanosaccharin 3 with aqueous alkali metal hydroxide solution

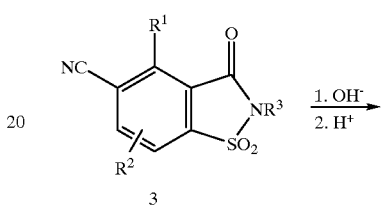

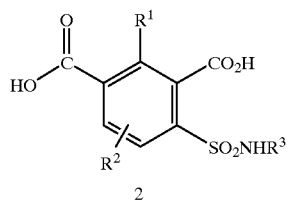

and subsequent addition of an acid.

3. A process as claimed in claim 2, wherein the 5-cyanosaccharin 3 is prepared by reaction of a dicyanobenzenesulfonyl chloride 4 with an amine of the formula R$^3$-NH$_2$ to give the iminosaccharin derivative 5

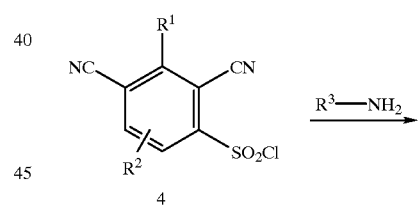

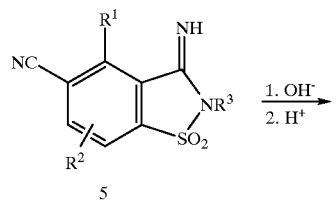

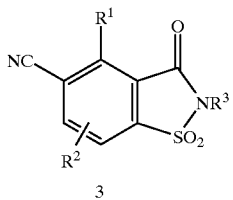

and subsequent acid hydrolysis.

4. A process as claimed in claim 1, wherein the inorganic acid halide used is thionyl chloride, phosphorus oxychloride, oxalyl chloride or phosgene.

5. A process as claimed in claim 1, wherein the reaction is carried out in an organic solvent.

6. A process as claimed in claim 5, wherein the reaction is carried out in toluene, chlorobenzene, xylenes or 1,2-dichloroethane.

7. A process as claimed in claim 1, wherein the reaction is carried out at 25–130° C.

8. A process as claimed in claim 2, wherein the alkali metal hydroxide solution used is sodium hydroxide or potassium hydroxide.

9. A process as claimed in claim 3, wherein the amine used is ammonia, $C_1$–$C_6$-alkylamine, $C_3$–$C_8$-cycloalkylamine, aniline or benzylamine which is optionally substituted in the phenyl ring by $C_1$–$C_4$-alkyl, halogen, $C_1$–$C_4$-haloalkyl or $C_1$–$C_4$-alkoxy.

10. A process as claimed in claim 9, wherein the amine used is methylamine, ethylamine or aniline.

* * * * *